(12) United States Patent
Ye et al.

(10) Patent No.: US 8,962,157 B2
(45) Date of Patent: Feb. 24, 2015

(54) ELECTRON-TRANSPORTING MATERIALS

(75) Inventors: Qing Ye, Los Gatos, CA (US); Jie Liu, Niskayuna, NY (US); Kelly Scott Chichak, Clifton Park, NY (US); Yangang Liang, Shanghai (CN)

(73) Assignee: General Electric Company, Schenectady, NY (US)

( * ) Notice: Subject to any disclaimer, the term of this patent is extended or adjusted under 35 U.S.C. 154(b) by 437 days.

(21) Appl. No.: 13/060,855

(22) PCT Filed: Aug. 19, 2009

(86) PCT No.: PCT/US2009/054241
§ 371 (c)(1),
(2), (4) Date: Feb. 25, 2011

(87) PCT Pub. No.: WO2010/036459
PCT Pub. Date: Apr. 1, 2010

(65) Prior Publication Data
US 2011/0155955 A1    Jun. 30, 2011

(30) Foreign Application Priority Data
Sep. 26, 2008    (CN) .......................... 2008 1 0161787

(51) Int. Cl.
| H01L 51/50 | (2006.01) |
| C09K 11/06 | (2006.01) |
| C07D 213/53 | (2006.01) |
| H01L 51/00 | (2006.01) |
| H05B 33/14 | (2006.01) |

(52) U.S. Cl.
CPC .............. C09K 11/06 (2013.01); C07D 213/53 (2013.01); H01L 51/0067 (2013.01); H01L 51/5048 (2013.01); H05B 33/14 (2013.01); C09K 2211/1007 (2013.01); C09K 2211/1029 (2013.01); Y10S 428/917 (2013.01)
USPC ........... 428/690; 428/917; 313/504; 313/505; 313/506; 257/40; 257/E51.05; 257/E51.026; 257/E51.032; 548/304.1; 548/418; 548/440; 548/444; 546/18; 546/79; 546/81; 546/101; 544/234

(58) Field of Classification Search
USPC .................. 428/690, 917; 313/504, 505, 506; 257/40, E51.032; 544/234; 546/18, 81
See application file for complete search history.

(56) References Cited

U.S. PATENT DOCUMENTS

| 7,777,043 | B2 | 8/2010 | Yabe et al. | |
| 2006/0186796 | A1* | 8/2006 | Yabe et al. | .................... 313/504 |
| 2008/0067922 | A1* | 3/2008 | Endo et al. | .................... 313/504 |
| 2009/0102356 | A1* | 4/2009 | Wang et al. | .................... 313/503 |

FOREIGN PATENT DOCUMENTS

| EP | 1555305 | A | 7/2005 | |
| JP | 07-325329 | | * 12/1995 | .............. C08F 34/00 |
| JP | 2000186066 | A | 7/2000 | |
| JP | 2005068078 | A | 3/2005 | |
| JP | 2005268199 | A | 9/2005 | |
| JP | 2008063232 | A | 3/2008 | |
| JP | 2008112984 | A | 5/2008 | |
| JP | 2008120696 | A | 5/2008 | |
| JP | 2008127326 | A | 6/2008 | |

OTHER PUBLICATIONS

Meier et al., Synthesis of Oligo(para-phenylene-meta-pyridinediyl)s, 2000, Journal fuer Organishe Chemie, 342(7), STN abstract.*
PCT Search Report and Written Opinion, dated Nov. 18, 2009.
(Continued)

Primary Examiner — Gregory Clark
(74) Attorney, Agent, or Firm — GE Global Patent Operation; Peter T. DiMauro

(57) ABSTRACT

Compounds of formula I may be used in optoelectronic devices

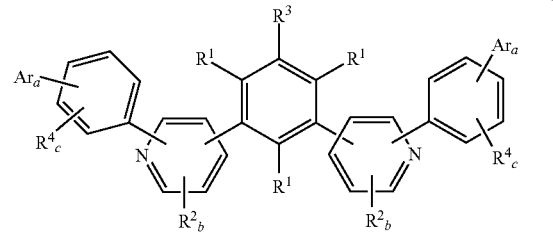

wherein
$R^1$, $R^2$ and $R^4$ are, independently at each occurrence, H, a $C_1$-$C_{20}$ aliphatic radical, a $C_3$-$C_{20}$ aromatic radical, or a $C_3$-$C_{20}$ cycloaliphatic radical;
$R^3$ is H or

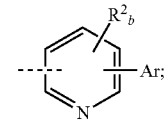

a is, independently at each occurrence, 1 or 2;
b is, independently at each occurrence, an integer ranging from 0-3;
c is, independently at each occurrence, an integer ranging from 0-4;
Ar is independently at each occurrence, H, or heteroaryl; and
at least two of Ar are heteroaryl.

21 Claims, No Drawings

(56) References Cited

OTHER PUBLICATIONS

Unofficial English translation of JP Office Action dated Dec. 3, 2013 from corresponding Application No. 2011-529049.
Su, Shi-Jian, et al., "Novel Four-Pyridylbenzene-Armed Biphenyls as Electron-Transport Materials for Phosphorescent OLEDs". Organic Letters, 2008, pp. 941-944, vol. 10, No. 5.

Unofficial English translation of CN Office Action dated Mar. 23, 2011 from corresponding Application No. 200810161787.4.

Unofficial English translation of CN Office Action dated Dec. 3, 2012 from corresponding Application No. 200810161787.4.

* cited by examiner

ELECTRON-TRANSPORTING MATERIALS

BACKGROUND

The invention relates generally to compounds, and particularly to compounds and optoelectronic devices using the same, as electron-transporting materials.

Optoelectronic devices, e.g. Organic Light Emitting Devices (OLEDs), which make use of thin film materials that emit light when subjected to a voltage bias, are expected to become an increasingly popular form of flat panel display technology. This is because OLEDs have a wide variety of potential applications, including cell phones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

OLEDs possess a sandwiched structure, which consists of one or more organic layers between two opposite electrodes. For instance, multi-layered devices usually comprise at least three layers: a hole injection/transport layer, an emissive layer and an electron transport layer (ETL). Furthermore, it is also preferred that the hole injection/transport layer serves as an electron blocking layer and the ETL as a hole blocking layer. Single-layered OLEDs comprise only one layer of materials between two opposite electrodes.

BRIEF DESCRIPTION

In one aspect, the invention relates to compounds of formula I:

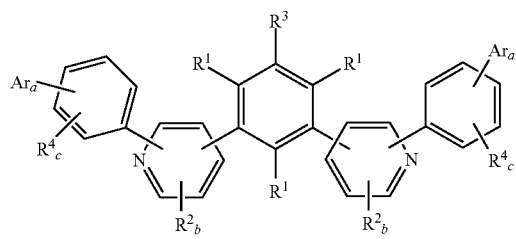

I wherein
$R^1$, $R^2$ and $R^4$ are, independently at each occurrence, H, a $C_1$-$C_{20}$ aliphatic radical.
a $C_3$-$C_{20}$ aromatic radical, or a $C_3$-$C_{20}$ cycloaliphatic radical;
$R^3$ is H or

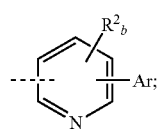

a is, independently at each occurrence, 1 or 2;
b is, independently at each occurrence, an integer ranging from 0-3;
c is, independently at each occurrence, an integer ranging from 0-4;
Ar is independently at each occurrence, H, or heteroaryl; and
at least two of Ar are heteroaryl, In another aspect, the invention relates to optoelectronic devices comprising at least one compound of formula I, particularly where the compound is present in an electron-transporting layer.

DETAILED DESCRIPTION

Compounds of formula I have properties useful in optoelectronic devices, e.g., organic light emitting devices (OLEDs), and are particularly well suited for use in electron-transporting layers thereof. The heteroaryl may be electron-withdrawing/electron deficient and may comprise multiple aromatic rings or a plurality of non-fused aromatic rings. The electron-withdrawing/electron deficient heteroaryl groups may be a pyridyl group, a pyrimidyl group, a quinolyl group, an isoquinolyl group, a phenanthranyl group, a indole group, an isoindole group, a carbazolyl group, aza-carbazolyl group, a thienyl group, a benzothienyl group, a thiazolyl group, a benzothiazolyl group, or a naphthyridinyl group, thienyl, furyl, pyridazinyl, pyrazinyl, thiazolyl and oxazolyl, etc. Ar may be pyridyl or phenylpyridyl.

In one aspect, the present invention relates to compounds of formula II and optoelectronic devices using the same:

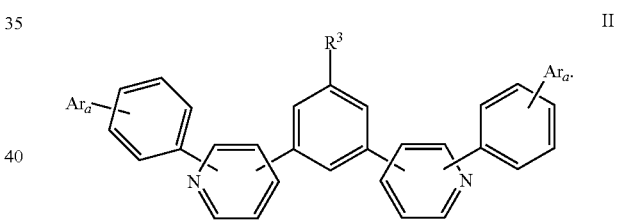

II

In another aspect, the present invention relates to compounds of formula III and optoelectronic devices using the same:

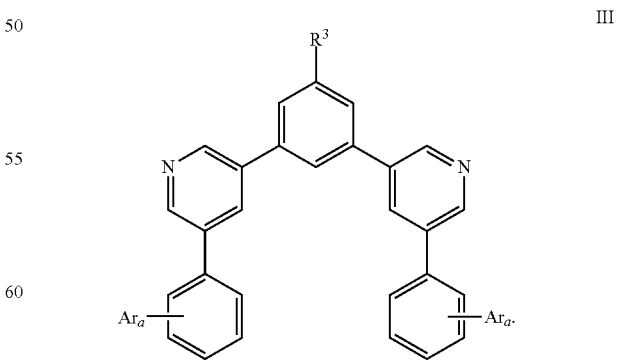

III

In yet another aspect, the present invention relates to compounds of formula IV-V and optoelectronic devices using any or any combination of them:

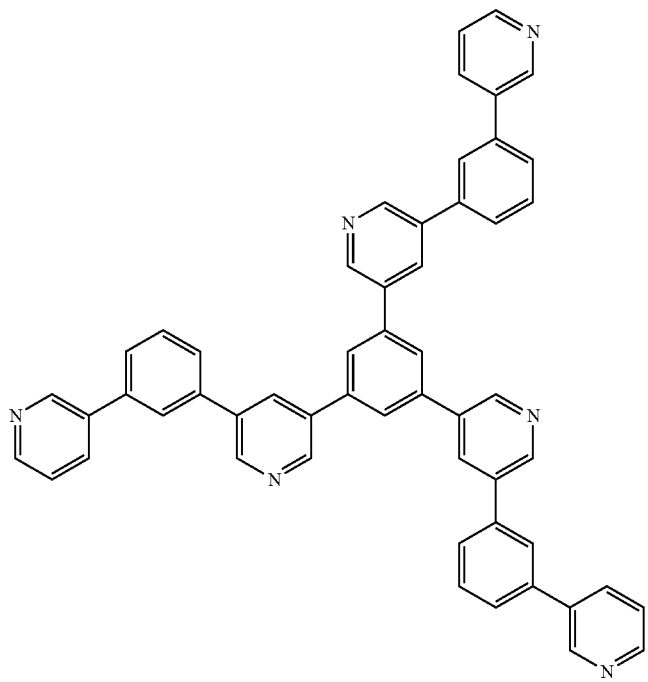

IV

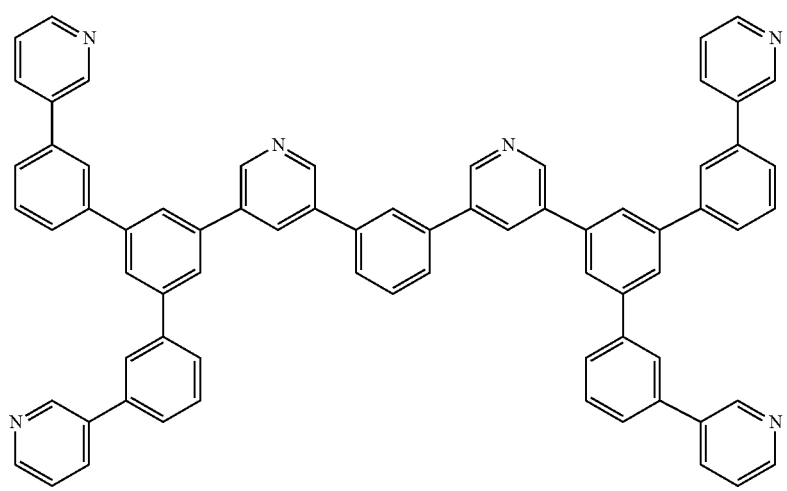

V

The compounds of formula I to V may be prepared by employing Suzuki cross-coupling reactions. The general procedure for Suzuki cross-coupling reactions includes mixing an aryl halide and aryl borate (or boronic acid) in a suitable solvent, in the presence of a base and Pd catalyst. The reaction mixture is heated under an inert atmosphere for a period of time. Suitable solvents include but are not limited to Dioxane, THF, EtOH, toluene and mixtures thereof. Exemplary bases include $Na_2CO_3$, $K_2CO_3$, $Cs_2CO_3$, Potassium phosphate and hydrates thereof. The bases can be added to the reaction as a solid powder or as an aqueous solution. The most commonly used catalysts include $Pd(PPh_3)_4$, or $Pd(OAc)_3$, $Pd(dba)_2$ with the addition of a secondary ligand. Exemplary ligands include dialkylphosphinobiphenyl ligands, such as structures VI-X shown below, in which Cy is cyclohexyl.

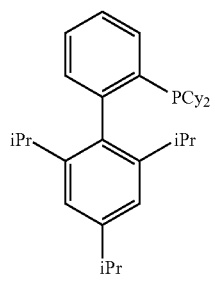

VI

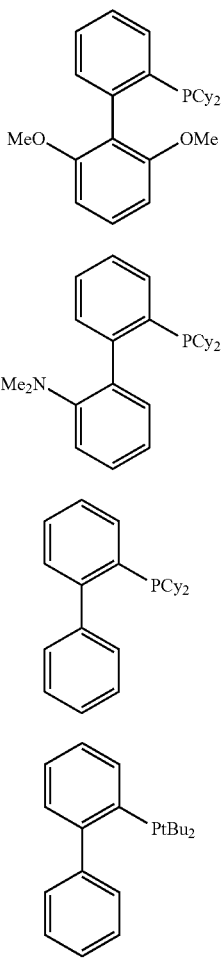

An optoelectronic device, e.g., an OLED, typically includes in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole blocking layer to prevent holes migrating toward the cathode. Additional components which may be present in an organic light-emitting device include hole transporting layers, hole transporting emission (emitting) layers and electron transporting emission (emitting) layers.

In one embodiment, the OLEDs comprising the organic compounds of the invention may be a fluorescent OLED comprising a singlet emitter. In another embodiment, the OLEDs comprising the organic compounds of the invention may be a phosphorescent OLED comprising at least one triplet emitter. In another embodiment, the OLEDs comprising the organic compounds of the invention comprise at least one singlet emitter and at least one triplet emitter. The OLEDs comprising the organic compounds of the invention may contain one or more, any or a combination of blue, yellow, orange, red phosphorescent dyes, including complexes of transition metals such as Ir, Os and Pt, In particular, electrophosphorescent and electrofluorescent metal complexes, such as those supplied by American Dye Source, Inc., Quebec, Canada may be used. Compounds of the formula I to V may be part of an emissive layer, or hole transporting layer or electron transporting layer, or electron injection layer of an OLED or any combination thereof.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e. holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode includes materials having a bulk resistivity of preferred about 1000 ohms per square, as measured by a four-point probe technique. Indium tin oxide (ITO) is frequently used as the anode because it is substantially transparent to transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to metals and metal oxides such as ITO etc which can inject negative charge carriers (electrons) into the inner layer(s) of the OLED. Various metals suitable for use as the cathode include K, Li, Na, Cs, Mg, Cu, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys, Layered non-alloy structures may also be employed in the cathode, such as a thin layer of a metal such as calcium, or a metal fluoride, such as LiF, covered by a thicker layer of a metal, such as aluminum or silver. In particular, the cathode may be composed of a single metal, and especially of aluminum metal.

Compounds of formula I to V may be used in electron transport layers in place of, or in addition to traditional materials such as poly(9,9-dioctyl fluorene), tris(8-hydroxyquinolato)aluminium (Alq$_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include 1,1-bis((di-4-tolylamino) phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino) benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis(4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use in the light emitting layer include electroluminescent polymers such as polyfluorenes, preferably poly(9,9-dioctyl fluorene) and copolymers thereof, such as poly(9,9'-dioctylfluorene-co-bis-N,N'-(4-butylphenyl) diphenylamine) (F8-TFB); poly(vinylcarbazole) and polyphenylenevinylene and their derivatives. In addition, the light emitting layer may include a blue, yellow, orange, green or red phosphorescent dye or metal complex, or a combination thereof. Materials suitable for use as the phosphorescent dye include, but are not limited to, tris(1-phenylisoquinoline) iridium (III) (red dye), tris(2-phenylpyridine) iridium (green dye) and Iridium (III) bis(2-(4,6-difluorephenyl)pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076R, ADS067RE, and ADS077RE.

Organic compounds of formula I to V may form part of the electron transport layer or electron injection layer or light emissive layer. Thus, in one aspect, the present invention relates to more efficient optoelectronic devices, e.g., ° LEDs comprising organic compounds of formula I to V. The OLEDs may be phosphorescent containing one or more, any or a combination of, blue, yellow, orange, green, red phosphorescent dyes.

DEFINITIONS

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n 2), and anthraceneyl groups (n=3). The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_{61}H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g. methyl salicyl), 2-nitromethylphen-1-yl (i.e., 2-NO$_2$CH$_2$Ph), 3-trimethylsilylphen-1-yl, 4-t-butylditnethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1- yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., $-C_6H_{10}C(CF_3)_2C_6H_{10}-$), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, bromopropylcyclohex-1-yloxy (e.g. $CH_3CHBrCH_2C_6H_{10}O-$), and the like. Further examples of cycloaliphatic radicals include 4-allyloxycyclohex-1-yl, 4-aminocyclohex-1-yl (i.e., $H_2C_6H_{10}-$) 4-aminocarbonylcyclopent-1-yl (i.e., $NH_2COC_5H_8-$), 4-acetyloxycyclohex-1-yl, 2,2-dicyanoisopropylidenebis(cyclohex-4-yloxy) (i.e., $-OC_6H_{10}C(CN)_2C_6H_{10}O-$), 3-methylcyclcohex-1-yl, methylenebis(cyclohex-4-yloxy) (i.e., $-OC_6H_{10}CH_2C_6H_{10}o-$), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., $-OC_6H_{10}(CH_2)_6(C_6H_{10}O-$), 4-hydroxymethylcyclohex-1-yl (i.e., $4-HOCH_2C_6N_{10}-$), 4-mercaptomethylcyclohex-1-yl (i.e., $4-HSCH_2C_6H_{10}-$), 4-methylthiocyclohex-1-yl (i.e., $4-CH_3SC_6H_{10}-$), 4-methoxycyclohex-1-yl, 2-methoxycarbonylcyclohex-1-yloxy ($2-CH_3OCOC_6H_{10}O-$), 4-nitromethylcyclohex-1-yl (i.e., $NO_2CH_2C_6H_{10}-$), 3-trimethylsilylcyclohex-1-yl, 2-t-butyldimethylsilylcyclopent-1-yl, 4-trimethoxysilylethylcylclohex-1-yl (e.g. $(CH_3O)_3SiCH_2CH_2C_6H_{10}-$), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O-$) represents a $C_4$ cycloaliphatic radical. The cyclohexylmethyl radical ($C_6H_{11}CH_2-$) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. $-CH_2CHBrCH_2-$), and the like. Further examples of aliphatic radicals include allyl, aminocarbonyl (i.e., $-CONH_2$), carbonyl, 2,2-dicyanoisopropylidene (i.e., $-CH_2C(CN)_2CH_2-$), methyl (i.e., $-CH_3$), methylene (i.e., $-CH_2-$), ethyl, ethylene, formyl (i.e., $-CHO$), hexyl, hexamethylene, hydroxymethyl (i.e. $-CH_2OH$), mercaptomethyl (i.e., $-CH_2SH$), methylthio, (i.e., $-SCH_3$), methylthiomethyl (i.e., $-CH_2SCH_3$), methoxy, methoxycarbonyl (i.e., $CH_3OCO-$), nitromethyl (i.e., $-CH_2NO_2$), thiocarbonyl, trimethylsilyl (i.e., $(CH_3)_3Si-$), t-butyldimethylsilyl, 3-trimethyoxysilylpropyl (i.e., $(CH_3O)_3SiCH_2CH_2CH_2-$), vinyl, vinylidene, and the like. By way of further example, a $C_1$-$C_{10}$ aliphatic radical contains at least one but no more than 10 carbon atoms. A methyl group (i.e., $CH-$) is an example of a $C_1$ aliphatic radical. A decyl group $CH_3(CH_2)_9-$) is an example of a $C_{10}$ aliphatic radical.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as an ether, methylene or ethylene moiety. The common linking group may also be a carbonyl as in phenyl pyridyl ketone. Examples of heteroaryl rings include thiophene, pyridine, isoxazole, pyrazole, pyrrole, furan, imidazole, indole, thiazole, benzimidazole, quinoline, isoquinoline, quinoxaline, pyrimidine, pyrazine, tetrazole, triazole, benzo-fused analogues of these groups, benzopyranone, phenylpyridine, tolylpyridine, benzothienylpyridine, phenylisoquinoline, dibenzoquinozaline, fluorenylpyridine, ketopyrrole, 2-phenylbenzoxazole, 2 phenylbenzothiazole, thienylpyridine, benzothienylpyridine, 3 methoxy-2-phenylpyridine, phenylimine, pyridylnaphthalene, pyridylpyrrole, pyridylimidazole, and phenylindole.

The term "aryl" is used herein to refer to an aromatic substituent which may be a single aromatic ring or multiple aromatic rings which are fused together, linked covalently, or linked to a common group such as an ether, methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 51) carbon atoms or between 3 and 20 carbon atoms.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Examples 1-8 describe the syntheses of compounds of formula IV-V, and intermediates used in making them. All reagents were purchased from Aldrich Chemical Co., Milwaukee, Wis., USA unless otherwise specified and were used without further purification. All compounds were characterized by $^1$H-NMR and found to correspond to the structures shown.

Example 1

Synthesis of Compound of Formula IV

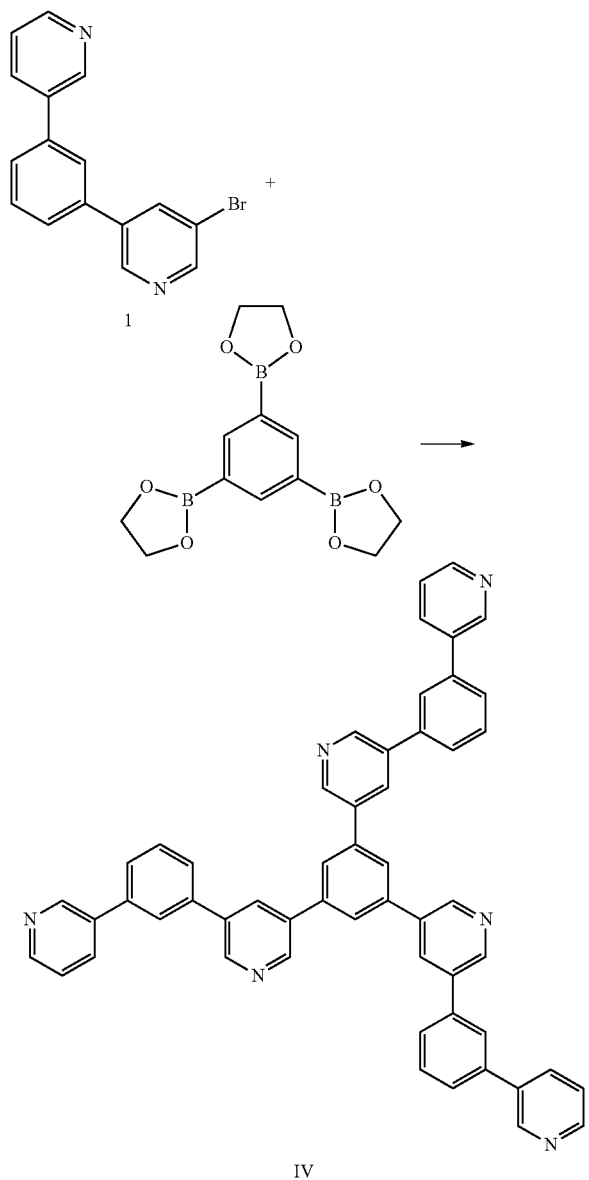

3-bromo-5-(3'-(3"-pyridyl phenyl)) pyridine (0.9 g, 29 mmol) and benzene-1,3,5-tris-ethyleneglycol boronate (0237 g, 0.83 mmol, molecular weight: 287.68) were added to a 50 mL of three neck round bottom flask. To this flask, dioxane (20 mL) and aqueous $K_2CO_3$ (2 N, 10 mL) were added. The mixture was stirred and degassed with a steam of argon for 15 minutes. Then under argon atmosphere, 0.03 of $Pd(PPH_3)_4$ was added. The mixture was brought to 80° C. and stirred overnight. The next day, solvent was removed by roto-evaporation and residue was suspended into an equal amount of water (20 mL) and $CH_2Cl_2$ (20 mL). The organic layer was separated from aqueous layer and washed with water (10 mL) and brine solution (10 mL). After dried over $Na_2SO_4$, and followed by removal of drying agent, organic solvent was removed by roto-evaporation. The residue was purified by column chromatography on silica gel, using 5% MeOH in $CH_2Cl_2$ as eluting solvent. Yield is 0.33 g, 50%. $^1$H NMR (δ, $CDCl_3$) 9.01 (d, 1H), 8.98 (d, 1H), 8.93 (d, 1H), 8.66 (d, 1H), 8.22 (t, 1H).

Example 2

Synthesis of Compound 1

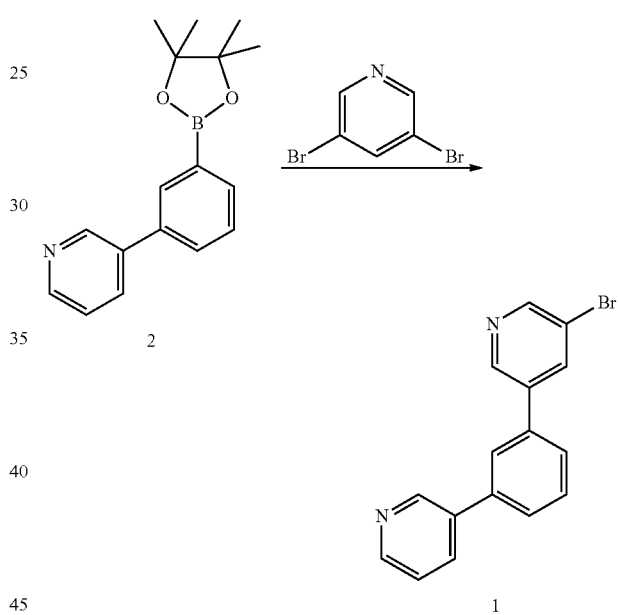

3-Pyridyl phenyl boronic acid pinacol ester (1.76 g, 6.26 mmol) and 1,3-dibromo pyridine (6.3 g, 31.3 mmol) were added to a 50 mL of three neck round bottom flask. To this flask, dioxane (20 mL) and aqueous $K_2CO_3$ (2 N, 10 mL were added. The mixture was stirred and degassed with a steam of argon for 30 minutes. Then under argon atmosphere, 0.05 g of $Pd(PPh_3)_4$ was added. The mixture was brought to 80° C. and stirred overnight. The next day, solvent was removed by roto-evaporation and residue was suspended into an equal amount of water (20 mL) and $C_2Cl_2$ (20 mL). The organic layer was separated from aqueous layer and washed with water (10 mL) and brine solution (10 mL). After dried over $Na_2SO_4$, and followed by removal of drying agent, organic solvent was removed by roto-evaporation. The residue was purified by column chromatography on silica gel, using Hexane/EtOAc as eluting solvent. Yield is 0.9 g, 50%. $^1$H NMR (δ, $CDCl_3$) 8.92 (d, 1H), 8.83 (d, 1H), 8.71 (d, 1H), 8.67 (dd, 1H), 8.09 (t, 1H), 7.94 (dt, 1H), 7.75 (s, 1H), 7.66 (m, 1H), 7.63 (m, 1H), 7.43 (dd, 1H).

Example 3

Synthesis of Compound 2

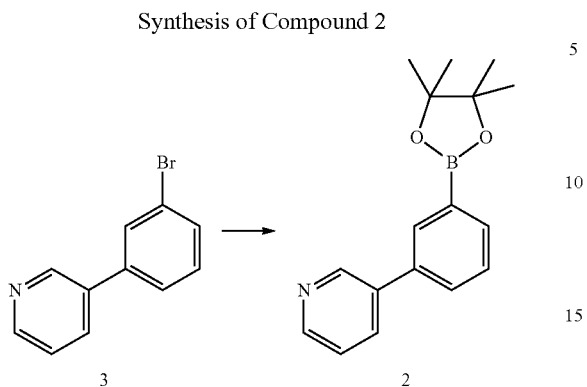

To a 3-neck round bottom flask fitted with a condenser, an argon inlet, and a rubber septum, were added compound 3 (1.8 g, 7.7 mmol), pinacolate diborane (5.86 g, 23.1 mmol), dry KOAc (2.26 g, 23.1 mmol), and 2-dicyclohexylphosphino-2',6'-dimethoxybiphenyl recrystallized from acetone (158.6 mg, 0.385 mmol). The flask was then placed under an argon atmosphere and was charged with anhydrous THF (30 mL), and the solution was degassed by purging argon through the stirred solution. After 15 minutes, the reaction mixture was charged with Pd(OAc)$_2$ (35.4 mg, 0.150 mmol) and the mixture was heated at 60° C. for overnight. The reaction mixture was then cooled to RT (room temperature) and filtered through a filter paper. The filter cake was washed with EtOAc and the filtrate was concentrated to dryness. The residue was column chromatographed through silica gel with a Hexane/EtOAc eluent. Yield was 90%. $^1$H NMR CDCl$_1$) 8.89 (d, 1H), 8.61 (dd, 1H), 8.05 (s, 1H), 7.94 (dt, 1H), 7.88 (d, 1H), 7.71 (d, 1H), 7.51 (t, 1H), 7.38 (dd, 1H), 1.39 (s, 12H).

Example 4

Synthesis of Compound 3

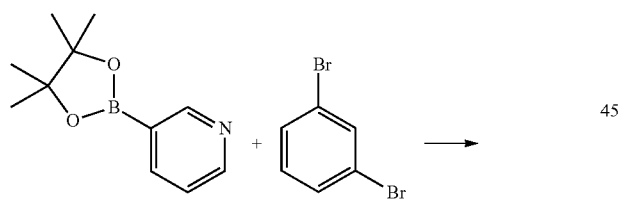

3-Pyridineboronic acid pinacol ester (8.7 g, 42.4 mmol) and 1,3-dibromo benzene (50.04 g, 212 mmol) were added to a 500 mL of three neck round bottom flask. To this flask, dioxane (250 mL) and aqueous K$_2$CO$_3$ (2 N, 125 mL) were added. The mixture was stirred and degassed with a steam of argon for 30 minutes. Then under, argon atmosphere, 1 g of Pd(PPh$_3$)$_4$ was added. The mixture was brought to 80° C. and stirred overnight. The next day, solvent was removed by rotoevaporation and residue was suspended into an equal amount of water (200 mL) and CH$_2$Cl$_2$ (200 mL). The organic layer was separated from aqueous layer and washed with water (100 mL) and brine solution (100 mL). After dried over Na$_2$SO$_4$, and removal of drying agent, some silica gel was added to the flask and the mixture was evaporated down to dryness. This silica gel absorbed with mixture of starting material and product was transferred to a medium fit preloaded with a bed of fresh silica gel. Hexane (1 L) was used to rinse the bed to afford un-reacted starting material. 1 L of ethyl acetated was rinsed to the silica gel bed, affording ~9 g of product. $^1$H NMR (CDCl$_3$) δ 8.83 (dd, 1H), 8.64 (dd, 1H), 7.86 (dt, 1H), 7.74 (t, 1H), 7.55 (dt, 1H), 7.52 (dt, 1H), 7.39 (dd, 1H), 7.37 (t, 1H).

Example 5

Synthesis of Compound of Formula V

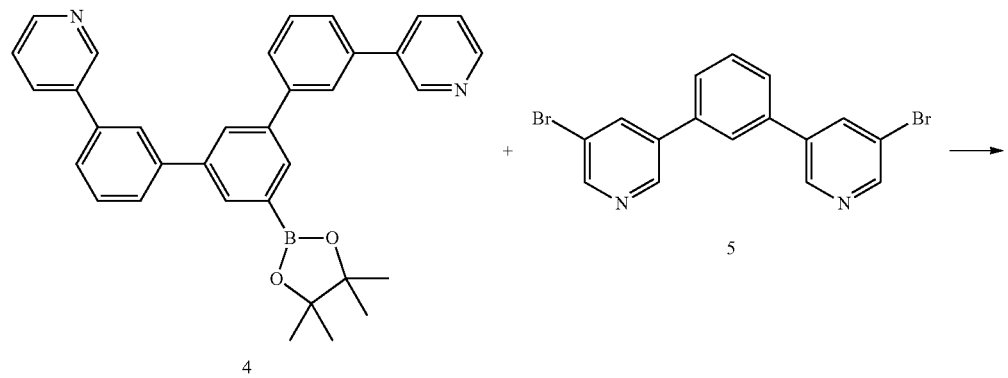

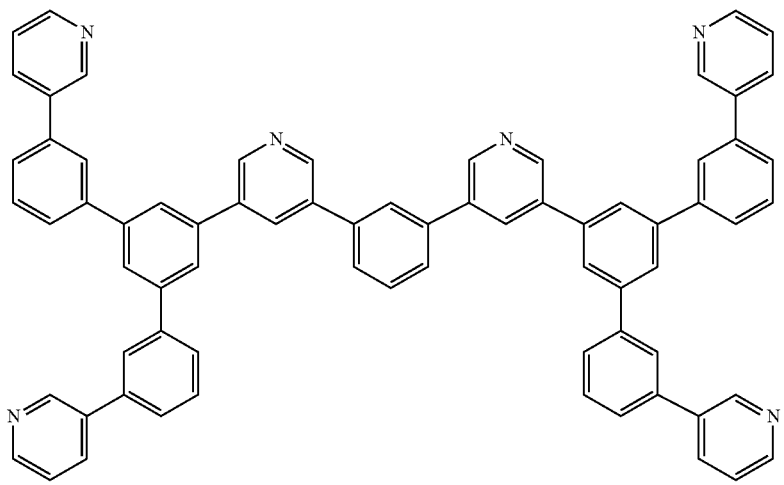

V

Compound 4 and compound 5 were added to dioxane and aqueous $K_2CO_3$. The mixture was stirred and degassed with a steam of argon for 15 minutes. Then under argon atmosphere a small amount of $Pd(PPh_3)_4$ was added. The mixture was brought to 80° C. and stirred overnight. After cooling to room temperature, the solution was filtered. Solvent was removed by roto-evaporation and residue was suspended into an equal amount of water and $CH_2Cl_2$. The organic layer was separated from aqueous layer and washed with water and brine solution. After dried over $Na_2SO_4$, and followed by removal of drying agent and organic solvent was removed by roto-evaporation. The residue was purified by column chromatography on silica gel, using 7% MeOH in $C_2Cl_2$ as eluting solvent. $^1H$ NMR (δ, $CDCl_3$) 9.00 (d, 1H), 8.96-8.93 (6H), 8.64 (t, 4H), 8.23 (t, 1H), 8.01-7.85 (tm, 13H), 7.81-7.58 (m, 15H), 7.42 (m, 41-1). MALDI 997.2838

Example 6

Synthesis of Compound 4

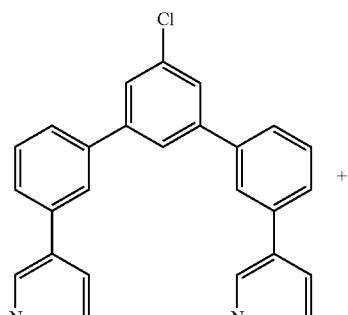

6

+

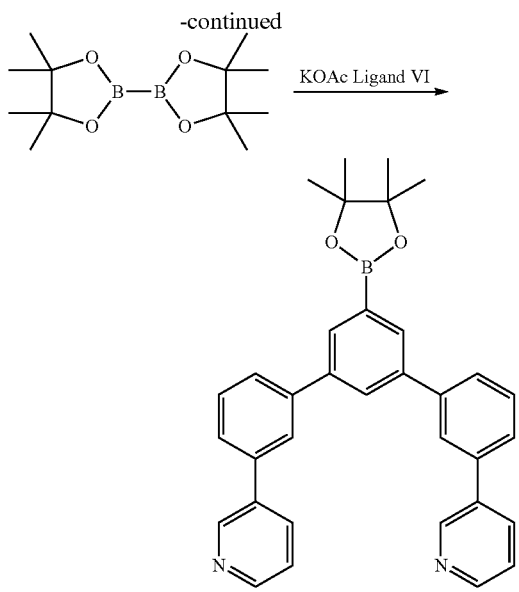

4

To a schlenk tube was charged compound 6 (0.419 g, 1 mmol), pinacolate diborane (0.762 g, 3 mmol), dry KOAc (0.294 g, 3 mmol), ligand VI (0.016 mg, 0.04 mmol) and $Pd(OAc)_2$ (13.46 mg, 0.02 mmol). The schlenk tube was evacuated and filled with argon three times. The schlenk was placed in a nitrogen box. 5 mL of anhydrous THF from the solvent distill was added. The flask was then sealed tightly and placed in an oil bath and heated at 60° C. for 4 days. After the reaction mixture was cooled to RT and filtered through a filter paper. The filter cake was washed with EtOAc and the filtrate was concentrated to dryness. The residue was column chromatographed through silica gel with EtOAc eluent. Yield was 65%. $^1$ NMR (δ, $CDCl_3$) 8.82 (s, 2H), 8.51 (s, 2H), 8.00 (d, 2H), 7.89 (m, 2H), 7.86 (t, 1H), 7.78 (s, 2H), 7.64 (m, 2H), 7.49 (m, 4H), 7.31 (dd, 2H), 1.29 (s, 12H).

Example 7

Synthesis of Compound 6

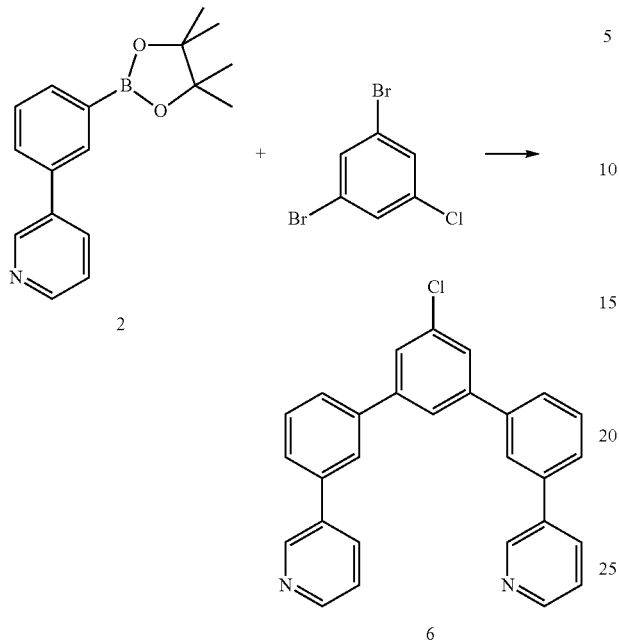

Compound 2 (0.6 g, 2.1 mmol) and 1,3-dibromo-5-chloro benzene (0.26 g, 0.97 mmol) were added to a 50 mL of three-neck round bottom flask. To this flask, dioxane (10 mL) and aqueous $K_2CO_3$ (2 N, 5 mL) were added. The mixture was stirred and degassed with a steam of argon for 15 min. Then under argon atmosphere 0.03 g of $Pd(PPh_3)_4$ was added. The mixture was brought to 80° C. and stirred overnight. The next day, solvent was removed by roto-evaporation and residue was suspended into an equal amount of water (10 mL) and $CH_2Cl_2$ (10 mL). The organic layer was separated from aqueous layer and washed with water (5 mL) and brine solution (5 mL). After dried over $Na_2SO_4$, and followed by removal of drying agent and organic solvent was removed by roto-evaporation. The residue was purified by column chromatography on silica gel, using EtOAc as eluting solvent. Yield is 0.25 g, 90%. $^1$H NMR (δ, $CDCl_3$) 8.92 (s, 2H), 8.64 (s, 2H), 7.94 (d, 2H), 7.80 (s, 2H), 7.75 (s, 1H), 7.63 (dd, t, 8H), 7.39 (dd, 2H).

Example 8

Synthesis of Compound 5

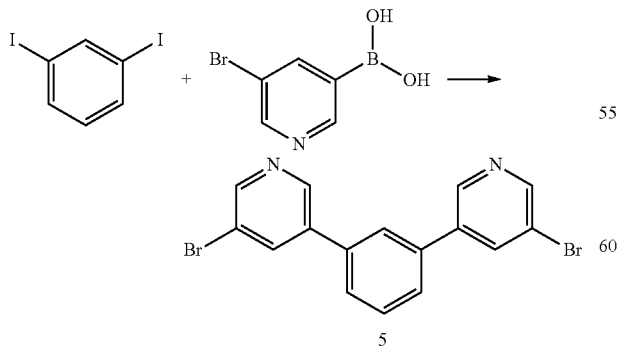

1,3-diiodo benzene (3.3 g, 10 mmol) and 3-bromo pyridine-5-boronic acid (6 g, 30 mmol) was added to dioxane (20 mL) and aqueous $K_2CO_3$ (2 N, 20 mL) was added. The mixture was stirred and degassed with a steam of argon for 15 min. Then under argon atmosphere a small amount of $Pd(PPh_3)_4$ was added. The mixture was brought to 80° C. and stirred overnight. After cooling to room temperature, the solution was filtered. Solvent was removed by roto-evaporation and residue was suspended into an equal amount of water (10 mL) and $CH_2Cl_2$ (10 mL). The organic layer was separated from aqueous layer and washed with water (5 mL) and brine solution (5 mL). After dried over $Na_2SO_4$, and followed by removal of drying agent and organic solvent was removed by roto-evaporation. The residue was purified by column chromatography on silica gel, using EtOAc as eluting solvent. Then the EtOAC solution was chilled in a refrigerator overnight and collected product as white powder, $^1$H NMR (δ, $CDCl_3$) 8.82 (d, 8.73 (d, 2H), 8.10 (t, 2H), 7.73 (s, 1H), 7.65 (s, 3H).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A compound of formula I

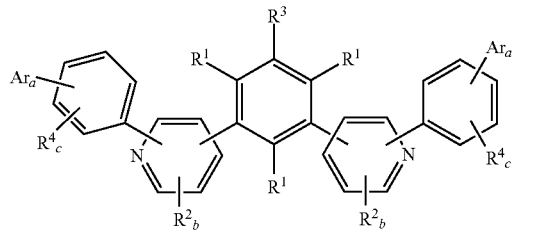

wherein
$R^1$, $R^2$ and $R^4$ are, independently at each occurrence, H, a $C_1$-$C_{20}$ aliphatic radical, a $C_3$-$C_{20}$ aromatic radical, or a $C_3$-$C_{20}$ cycloaliphatic radical;
$R^3$ is H or

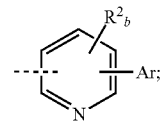

a is, independently at each occurrence, 1 or 2;
b is, independently at each occurrence, an integer ranging from 0-3;
c is, independently at each occurrence, an integer ranging from 0-4;
Ar is independently at each occurrence, H, or heteroaryl; and
at least two of Ar are heteroaryl; and
said heteroaryl is selected from one of a pyridyl group, a phenylpyridyl, a pyrimidyl group, a quinolyl group, an isoquinolyl group, an electron-withdrawing and electron deficient heteroaryl phenanthranyl group, a indole group, an isoindole group, a thienyl group, a benzothienyl group, a thiazolyl group, a benzothiazolyl group, a naphthyridinyl group, thienyl, furyl, pyridazinyl, pyrirnidinyl, pyrazinyl, thiazolyl and oxazolyl.

2. The compound of claim 1, being of formula

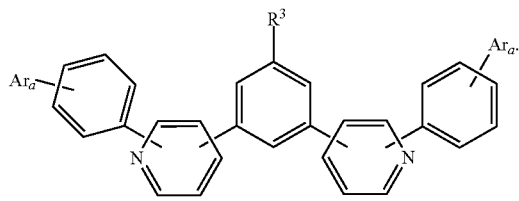

3. The compound of claim 1, being of formula

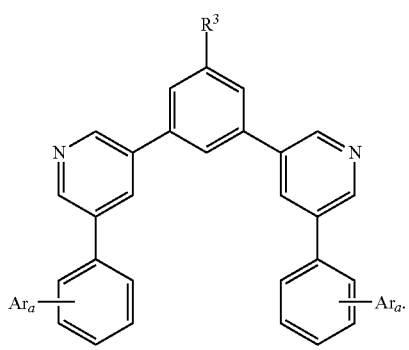

4. The compound of claim 1, wherein the heteroaryl comprises multiple aromatic rings.

5. The compound of claim 1, wherein the heteroaryl comprises a plurality of non-fused aromatic rings.

6. The compound of claim 1, wherein Ar is pyridyl or phenylpyridyl.

7. The compound of claim 1, wherein Ar is pyridyl.

8. The compound of claim 1, wherein Ar is phenylpridyl.

9. The compound of claim 1, wherein $R^3$ is

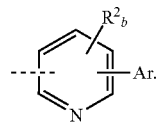

10. The compound of claim 1, wherein $R^3$ is H.

11. The compound of claim 1, wherein the heteroaryl is elecetron-withdrawing.

12. The compound of claim 1, being of formula

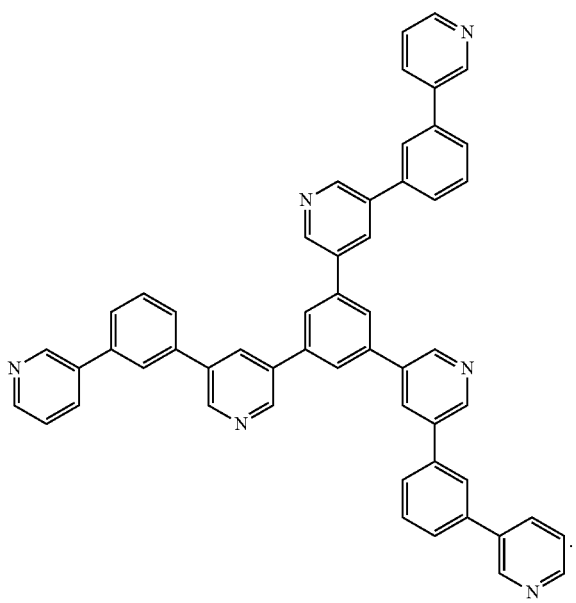 [SMILES: c1cncc(-c2cccc(-c3cncc(-c4cc(-c5cncc(-c6cccc(-c7cccnc7)c6)c5)cc(-c5cncc(-c6cccc(-c7cccnc7)c6)c5)c4)c3)c2)c1]

13. The compound of claim 1, being of formula

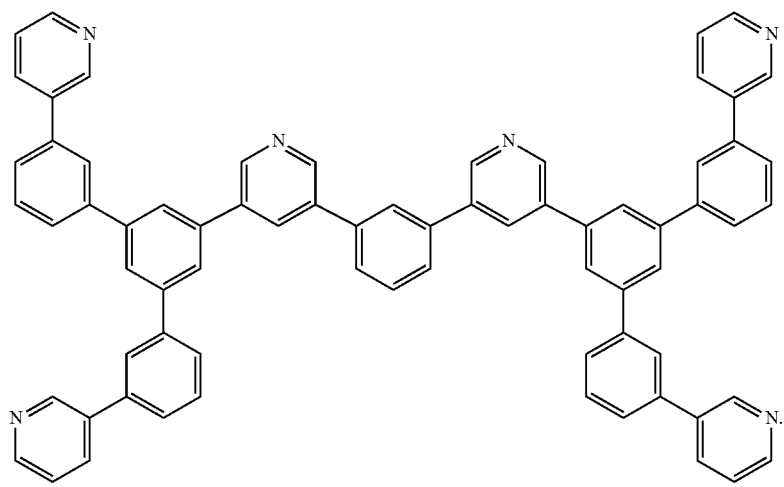 [SMILES: c1cncc(-c2cccc(-c3cc(-c4cccc(-c5cccnc5)c4)cc(-c4cncc(-c5cccc(-c6cncc(-c7cc(-c8cccc(-c9cccnc9)c8)cc(-c8cccc(-c9cccnc9)c8)c7)c6)c5)c4)c3)c2)c1]

14. An optoelectronic device comprising a compound of formula I

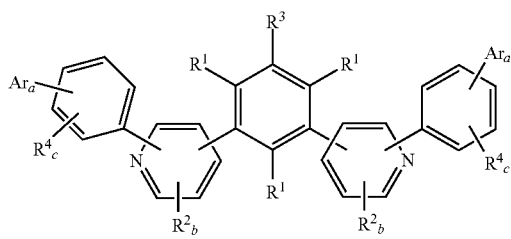

wherein
R$^1$, R$^2$ and R$^4$ are, independently at each occurrence, H, a C$_1$-C$_{20}$ aliphatic radical, a C$_3$-C$_{20}$ aromatic radical, or a C$_3$-C$_{20}$ cycloaliphatic radical;
R$^3$ is H or

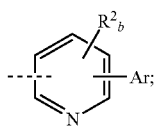

a is, independently at each occurrence, 1 or 2;
b is, independently at each occurrence, an integer ranging from 0-3;
c is, independently at each occurrence, an integer ranging from 0-4;
Ar is independently at each occurrence, H, or heteroaryl; and
at least two of Ar are heteroaryl; and
said heteroaryl is selected from one of a pyridyl group, a phenylpyridyl, a pyrimidyl group, a quinolyl group, an isoquinolyl group, an electron-withdrawing and electron deficient heteroaryl phenanthranyl group, a indole group, an isoindole group, a thienyl group, a benzothienyl group, a thiazolyl group, a benzothiazolyl group, a naphthyridinyl group, thienyl, furyl, pyridazinyl, pyrazinyl, thiazolyl and oxazolyl.

15. The optoelectronic device of claim 14, comprising a compound of formula

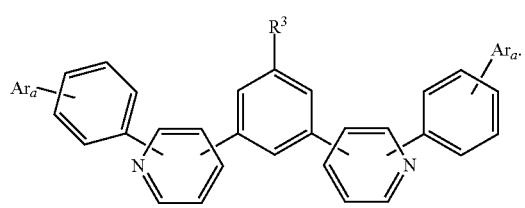

16. The optoelectronic device of claim 14, comprising a compound of formula

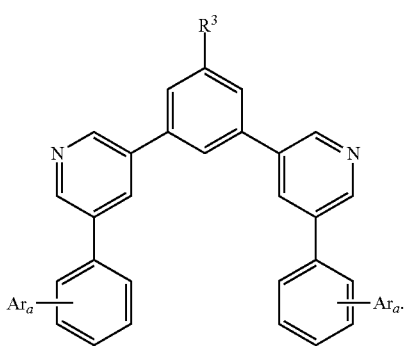

17. The optoelectronic device of claim 14, wherein the compound is of formula

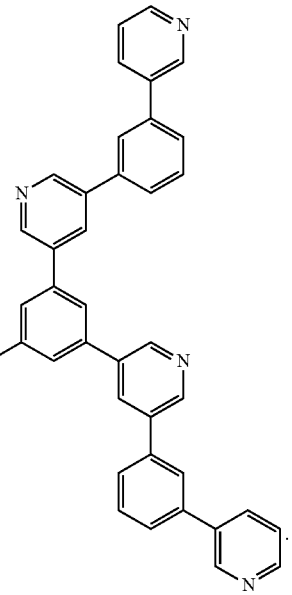

18. The optoelectronic device of claim 14, wherein the compound is of formula

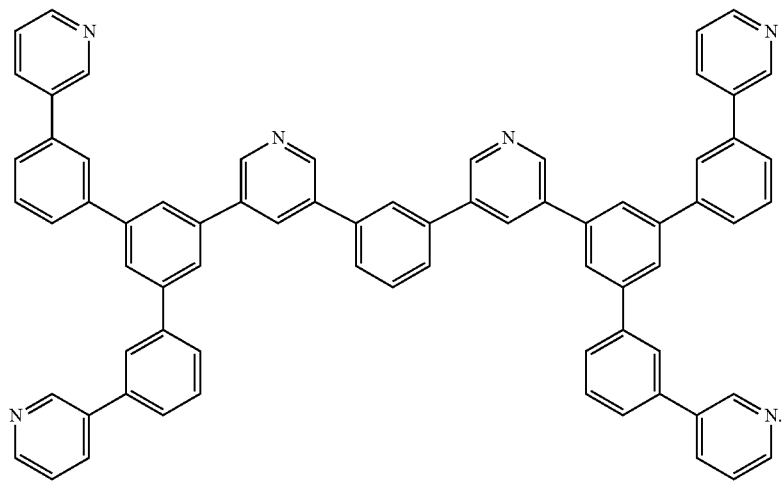 [SMILES: c1cncc(-c2cccc(-c3cc(-c4cccc(-c5cccnc5)c4)cc(-c4cncc(-c5cccc(-c6cncc(-c7cc(-c8cccc(-c9cccnc9)c8)cc(-c8cccc(-c9cccnc9)c8)c7)c6)c5)c4)c3)c2)c1]
19. The optoelectronic device of claim 14, comprising one or more fluorescent emissive materials.
20. The optoelectronic device of claim 14, comprising one or more phosphorescent emissive materials,
21. The optoelectronic device of claim 14, comprising one or more, any or a combination of blue, yellow, orange, green and red phosphorescent dyes.
* * * * *

UNITED STATES PATENT AND TRADEMARK OFFICE
CERTIFICATE OF CORRECTION

PATENT NO. : 8,962,157 B2
APPLICATION NO. : 13/060855
DATED : February 24, 2015
INVENTOR(S) : Ye et al.

It is certified that error appears in the above-identified patent and that said Letters Patent is hereby corrected as shown below:

In the Specification

In Column 1, Line 7, delete "same," and insert -- same, e.g., --, therefor.

In Column 1, Line 55, delete "radical." and insert -- radical, --, therefor.

In Column 2, Line 8, delete "heteroaryl," and insert -- heteroaryl. --, therefor.

In Column 2, Line 29, delete "pyridazinyl," and insert -- pyridazinyl, pyrimidinyl, --, therefor.

In Column 3, Line 64, delete "or Pd(OAc)$_3$," and insert -- or Pd(OAc)$_2$, --, therefor.

In Column 6, Line 6, delete "Pt," and insert -- Pt. --, therefor.

In Column 6, Line 51, delete "transmission" and insert -- light transmission --, therefor.

In Column 6, Line 61, delete "Cu," and insert -- Ca, --, therefor.

In Column 6, Line 64, delete "alloys," and insert -- alloys. --, therefor.

In Column 7, Line 52, delete "° LEDs" and insert -- OLEDs --, therefor.

In Column 8, Line 6, delete "(n 2), and anthraceneyl" and insert -- (n=2), and anthracenyl --, therefor.

In Column 8, Line 12, delete "(C$_{61}$H$_3$)" and insert -- (C$_6$H$_3$) --, therefor.

In Column 8, Line 36, delete "phenylethenyl," and insert -- phenylethenyl, 3-formyl-2-thienyl, --, therefor.

Signed and Sealed this
Seventeenth Day of November, 2015

Michelle K. Lee
*Director of the United States Patent and Trademark Office*

CERTIFICATE OF CORRECTION (continued)
U.S. Pat. No. 8,962,157 B2

In Column 9, Line 18, delete "(i.e., $H_2C_6H_{10}$-)" and insert -- (i.e., $H_2NC_6H_{10}$-) --, therefor.

In Column 10, Line 14, delete "(i.e., CH-)" and insert -- (i.e., $CH_3$-) --, therefor.

In Column 10, Line 58, delete "3 and 51)" and insert -- 3 and 50 --, therefor.

In Column 12, Line 1, delete "(0.9 g, 29" and insert -- (0.9 g, 2.9 --, therefor.

In Column 12, Line 2, delete "(0237" and insert -- (0.237 --, therefor.

In Column 12, Line 7, delete "0.03" and insert -- 0.03 g --, therefor.

In Column 12, Line 17, delete "8.22 (t, 1H)." and insert -- 8.22 (t, 1H), 7.98 (s, 1H), 7.96 (dt, 1H), 7.86 (bs, 1H), 7.74 (dt, 1H), 7.68 (bm, 2H), 7.42 (dd, 1H). --, therefor.

In Column 12, Line 51, delete "(2 N, 10 mL" and insert -- (2 N, 10 mL) --, therefor.

In Column 12, Line 57, delete "$C_2Cl_2$ (20 mL)." and insert -- $CH_2Cl_2$ (20 mL). --, therefor.

In Column 13, Line 34, delete "$^1$H NMR $CDCl_1$)" and insert -- $^1$H NMR ($\delta$, $CDCl_3$) --, therefor.

In Column 14, Line 24, delete "under," and insert -- under --, therefor.

In Column 14, Line 36, delete "fit" and insert -- frit --, therefor.

In Column 15, Line 40, delete "$C_2Cl_2$" and insert -- $CH_2Cl_2$ --, therefor.

In Column 15, Line 43, delete "MALDI 997.2838" and insert -- MALDI (M+) 997.2838. --, therefor.

In Column 18, Line 16, delete "8.82 (d," and insert -- 8.82 (d, 2H), --, therefor.

In the Claims

In Column 18, Line 66, in Claim 1, delete "pyrirnidinyl," and insert -- pyrimidinyl, --, therefor.

In Column 20, Line 12, in Claim 11, delete "elecetron-withdrawing." and insert -- electron-withdrawing. --, therefor.

In Column 23, Line 25, in Claim 20, delete "materials," and insert -- materials. --, therefor.